(12) United States Patent
Honma et al.

(10) Patent No.: US 9,186,260 B2
(45) Date of Patent: Nov. 17, 2015

(54) IMPLANT AND IMPLANT ASSEMBLY

(71) Applicant: Terumo Kabushiki Kaisha, Tokyo (JP)

(72) Inventors: Yasuyuki Honma, Kanagawa (JP); Yuji Nakagawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/219,867

(22) Filed: Mar. 19, 2014

(65) Prior Publication Data

US 2014/0243984 A1      Aug. 28, 2014

Related U.S. Application Data

(63) Continuation of application No. PCT/JP2012/081182, filed on Nov. 30, 2012.

(30) Foreign Application Priority Data

Dec. 2, 2011    (JP) ................................ 2011-265238

(51) Int. Cl.
*A61F 2/44* (2006.01)
*A61B 17/70* (2006.01)
*A61B 17/16* (2006.01)

(52) U.S. Cl.
CPC .............. *A61F 2/442* (2013.01); *A61B 17/1604* (2013.01); *A61B 17/1671* (2013.01); *A61B 17/7065* (2013.01); *A61B 17/7097* (2013.01)

(58) Field of Classification Search
CPC ........... A61B 17/7065; A61B 17/7067; A61B 17/7097
See application file for complete search history.

(56) References Cited

U.S. PATENT DOCUMENTS

| 6,733,533 | B1 | 5/2004 | Lozier | |
|---|---|---|---|---|
| 6,733,534 | B2 * | 5/2004 | Sherman | 623/17.16 |
| 6,958,077 | B2 * | 10/2005 | Suddaby | 623/17.11 |
| 8,540,752 | B2 * | 9/2013 | de Moura | 606/249 |
| 8,814,908 | B2 * | 8/2014 | Druma et al. | 606/248 |

(Continued)

FOREIGN PATENT DOCUMENTS

| JP | 2002-516697 A | 6/2002 |
|---|---|---|
| JP | 2004-167254 A | 6/2004 |
| JP | 2009-082726 A | 4/2009 |

(Continued)

OTHER PUBLICATIONS

International Search Report mailed Jan. 22, 2013 in related International Application PCT/JP2012/081182 with English-language translation (4 pgs.).

*Primary Examiner* — Ellen C Hammond
(74) *Attorney, Agent, or Firm* — Foley & Lardner LLP

(57) ABSTRACT

An implant configured to be placed in a living body to be expansively deformed and contractively deformed comprises a first layer that forms a filling unit that is configured to be filled with a filling material to maintain an expanded state of the implant, the first layer comprising a porous membrane; a second layer that covers the first layer, the second layer comprising at least one of (i) a fluid-impermeable membrane, and (ii) a gas-permeable porous membrane that is impermeable by liquids or gels; and an introduction port that communicates with the filling unit and is configured to introduce the filling material into the filling unit. An introduction region is formed between the first layer and the second layer, the introduction region being configured to receive a fluid permeating the first layer when the filling material is introduced into the filling unit.

9 Claims, 12 Drawing Sheets

(56) References Cited

U.S. PATENT DOCUMENTS

| | | |
|---|---|---|
| 2002/0156482 A1 | 10/2002 | Scribner et al. |
| 2005/0131267 A1 | 6/2005 | Talmadge |
| 2010/0249841 A1* | 9/2010 | Trieu et al. .................... 606/249 |
| 2012/0209329 A1* | 8/2012 | Hata et al. .................... 606/249 |

FOREIGN PATENT DOCUMENTS

| WO | WO-2009/006258 A1 | 1/2009 |
|---|---|---|

* cited by examiner

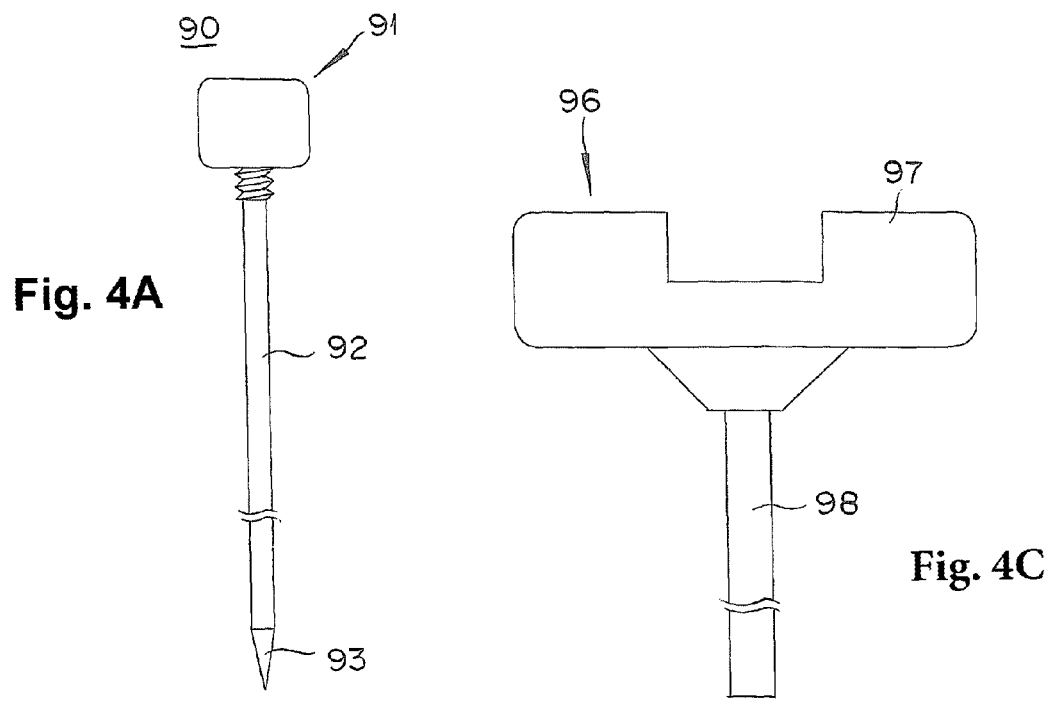
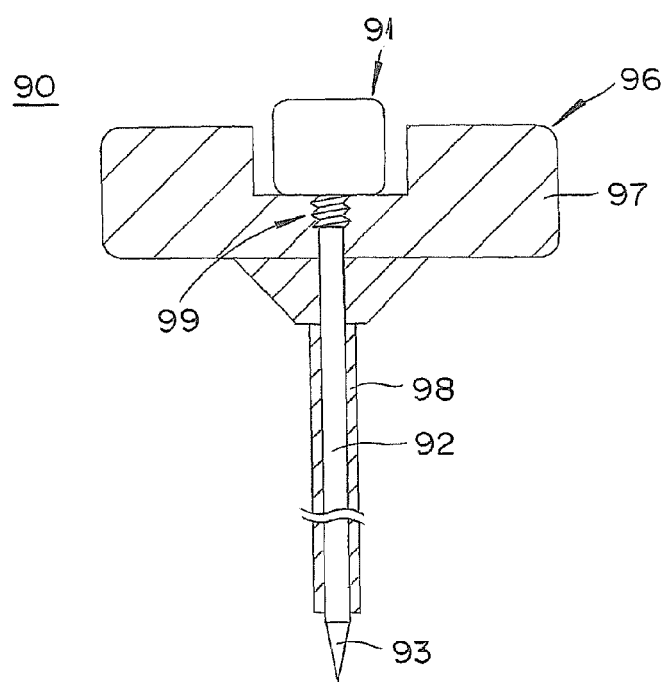

IMPLANT AND IMPLANT ASSEMBLY

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/081182 filed on Nov. 30, 2012, which is based upon and claims the benefit of priority of Japanese Application No. 2011-265238 filed on Dec. 2, 2011, the entire contents of which are hereby incorporated by reference in its entirety.

BACKGROUND

1. Technical Field

The disclosure relates to an implant that is placed into a living body, and an implant assembly that includes the implant.

2. Background Art

In the medical field, techniques relating to implants that are placed into living bodies and various techniques relating to methods for placing the implants into the living bodies are known. For example, International Publication No. WO 2009/006258 discloses an implant that is placed between spinous processes of the living body to treat lumbar spinal canal stenosis.

In the related art, an expansively deformable balloon is injected with a filling material and the balloon is used as an implant for spacing between the spinous processes. The balloon injected with the filling material causes the distance between the adjacent spinous processes to be expanded and maintained with a predetermined gap. The balloon functions as a spacer which is placed in the living body over a long period of time. A relatively rigid material is sometimes used as the filling material so as to maintain an expanded state of the balloon over a long period of time. However, when the rigidity of the filling material is high, a load on the spinous processes and living body tissue present around the spinous processes increases, and thus, this type of implant is not suitable to be placed in the living body over a long period of time.

U.S. Patent Publication No. 2010/0249841 discloses an implant for spinous processes that includes an inner side container forming a space to hold the filling material and an outer side container which is arranged in an overlapping manner so as to cover a part of an outer circumferential surface of the inner side container. This implant is capable of addressing the problem of WO 2009/006258 described above by filling the inner side container with the filling material and filling the outer side container with a relatively flexible material. However, in order to allow the inner side container to be filled with the filling material and additionally allow the relatively flexible material to be introduced into the outer side container, a plurality of introduction paths (catheters and the like) must be used to communicate with the respective containers. When the plurality of introduction paths are used, a larger wound hole must be formed in the living body during the introduction of the implant into the living body, which is problematic in that the introduction of the implant cannot be performed in a minimally invasive manner.

Therefore, there is a need for an implant which can be introduced into the living body in a minimally invasive manner and can reduce the load on the living body while in use regardless of the type of the filling material used to maintain the expanded state, and an implant assembly including the implant.

SUMMARY OF INVENTION

In one embodiment, an implant that is placed in a living body and can be expansively deformed and contractively deformed includes a first layer that is formed from a porous membrane which partitions a filling unit filled with a filling material to maintain an expanded state of the implant, a second layer that is formed from a fluid-impermeable membrane or a gas-permeable porous membrane which is impermeable by a liquid and gel among the fluids and is arranged to cover the first layer, and an introduction port that communicates with the filling unit and introduces the filling material into the filling unit, in which an introduction region into which the fluid permeating the first layer is introduced with introduction of the filling material into the filling unit is partitioned between the first layer and the second layer.

In one aspect, a solid or a hardening material being fluid at a time of the introduction into the filling unit and hardening after the introduction is used as the filling material, and a porous membrane that is not permeated by the filling material is used in the first layer.

In one aspect, at least one of a material constituting the first layer and a material constituting the second layer has a fiber material.

In one aspect, the second layer is coated with a water-swellable polymer material.

In one aspect, the implant further includes connection members that connect the first layer and the second layer with each other to position relative positions of the first layer and the second layer.

In one aspect, at least the first layer and the second layer are connected with each other by the introduction port forming the connection member.

In one aspect, at least a body section that extends in a longitudinal direction and a wide section that has a greater width than the body section are formed in the implant after the expansive deformation, and the connection members have at least one of a body section side connection member that connects the first layer and the second layer with each other in the body section and a wide section side connection member that connects the first layer and the second layer with each other in the wide section.

In one aspect, the connection members are disposed in pairs at opposing positions of the implant.

In one embodiment, an implant assembly includes an implant, a tubular member that includes a distal end section which is inserted into the filling unit of the implant via the introduction port, an opening section that is disposed in the distal end section to introduce the filling material into the filling unit, and a lumen that communicates with the opening section.

In one aspect, a volume of the lumen of the tubular member is formed to be equal to a volume of the introduction region or larger than the volume of the introduction region.

According to embodiments of the present invention, the fluid that functions as the buffer material can be held in the introduction region partitioned to cover the filling unit, and thus the load onto the living body while in use can be reduced regardless of the type of the filling material used to maintain the expanded state of the implant. Also, the fluid present in the filling unit can be introduced into the introduction region with the introduction of the filling material into the filling unit, and thus an introduction path to introduce the fluid into the introduction region does not have to be disposed in addition to an introduction path to introduce the filling material into the filling unit. Accordingly, the introduction of the implant into the living body can be performed in a minimally invasive manner.

BRIEF DESCRIPTION OF DRAWINGS

FIG. 3A is a view showing a state before the introduction port and the filling member are connected with each other, FIG. 3B is a view showing a state where the introduction port and the filling member are connected with each other, and FIG. 3C is a partially enlarged view of a part shown by a dashed line part 3C of FIG. 3A.

FIGS. 4A-4C are views illustrating a puncture tool that is used to introduce the implant into a living body. FIG. 4A is a view showing an inner needle of the puncture tool, FIG. 4C is a view showing an outer needle of the puncture tool, and FIG. 4B is a view showing a state where the inner needle and the outer needle are assembled and integrated with each other.

FIG. 5A is a simplified view showing a lumbar part of the living body, FIG. 5B is an enlarged view showing a spinal column, and FIG. 5C is an arrow view of a lumbar vertebra seen from an arrow 5C direction of FIG. 5B.

FIG. 6A is a view showing a state before the puncture tool is punctured into the living body, and FIG. 6B is a view showing a state where the puncture tool is punctured into the living body.

FIG. 7A is a view showing a state where the implant is positioned between the spinous processes, and FIG. 7B is a view showing a state where the implant is expanded between the spinous processes.

FIG. 8A is a plan view showing the implant with the spinous processes, and FIG. 8B is a front view showing the implant with the spinous processes.

FIG. 9A is a schematic view of the implant that is expanded by an introduction of the filling material, and FIG. 9B is a schematic view showing the implant after the expansive deformation.

FIG. 10A is a schematic view of the implant that is expanded by an introduction of a contrast agent, and FIG. 10B is a schematic view of the implant after the expansive deformation which is expanded by the contrast agent.

FIG. 11A is a schematic view showing the implant that is expanded by an introduction of a liquid and gel, and FIG. 11B is a schematic view showing the implant after the expansive deformation which is expanded by the filling material.

FIG. 12A is a simplified view showing a first shape example of the implant, FIG. 12B is a simplified view showing a second shape example of the implant, and FIG. 12C is a simplified view showing a third shape example of the implant.

DETAILED DESCRIPTION

Figure 1:
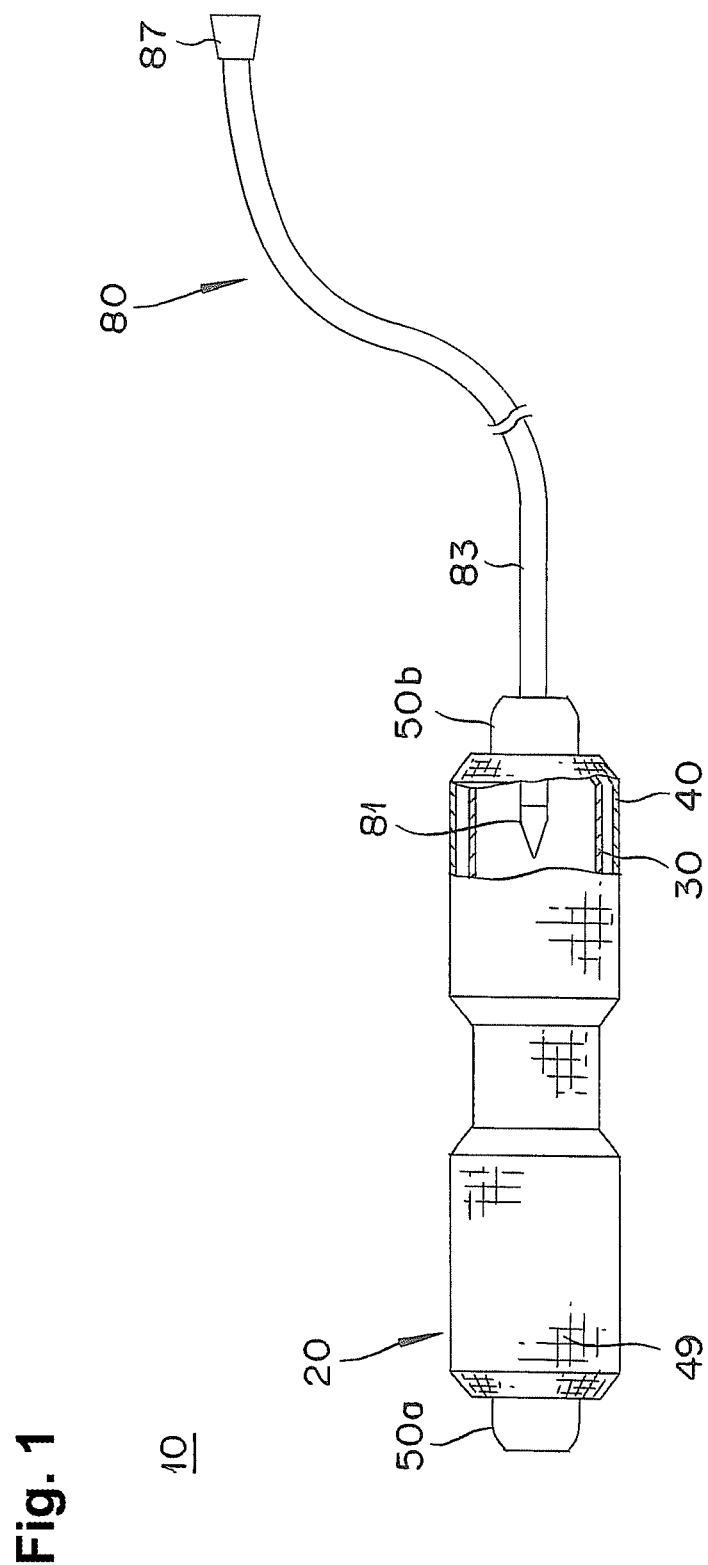
FIG. 1 is a partial cross-sectional view showing an overall configuration of an implant assembly according to an embodiment of the present invention with an implant before an expansive deformation.

Hereinafter, embodiments of the present invention will be described based on the accompanying drawings. In the description of the drawings, the same reference numerals are used to designate the same components and redundant descriptions thereof are omitted. In some cases, dimensional ratios in the drawings are exaggerated and are different from the actual ratios for the convenience of description.

Figure 2:
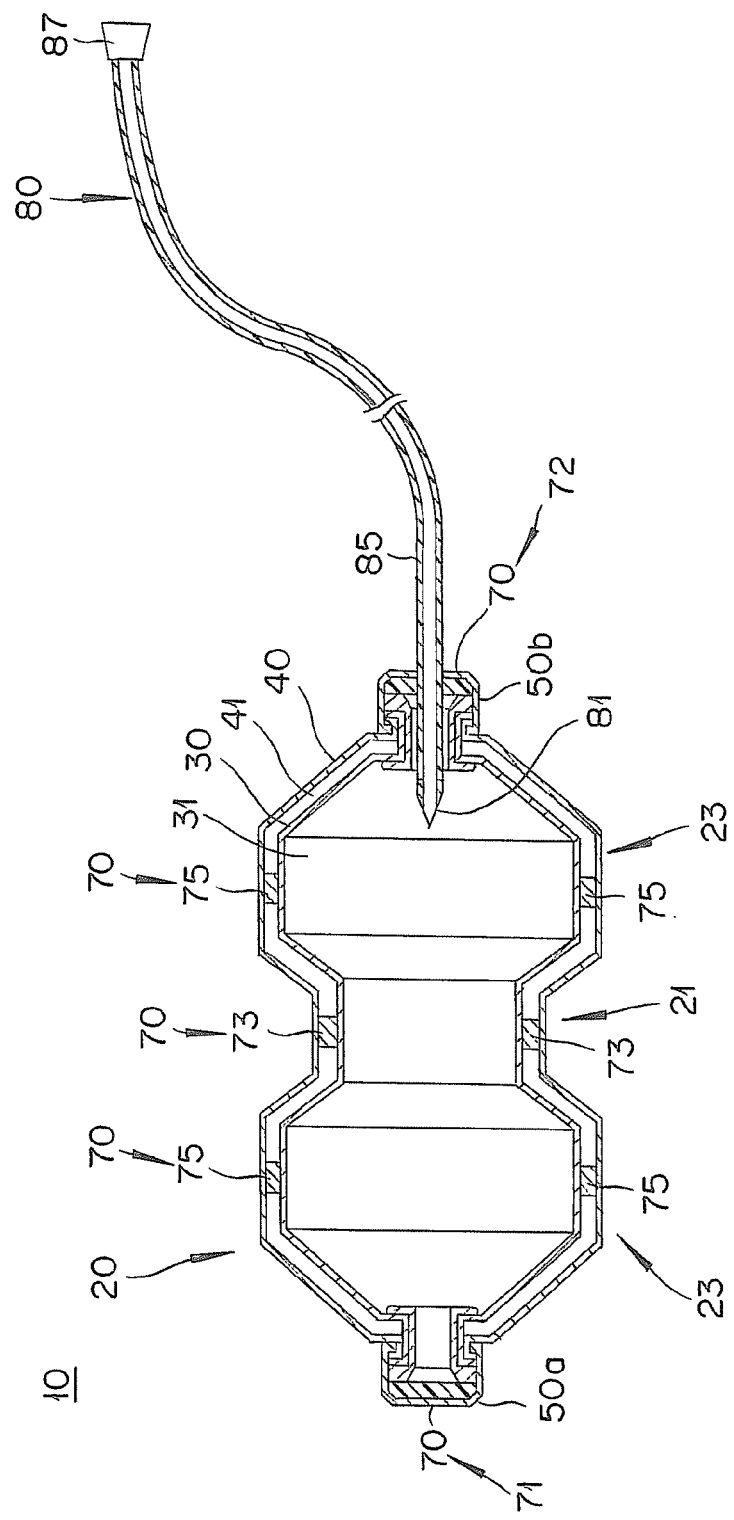
FIG. 2 is a cross-sectional view showing the overall configuration of the implant assembly according to the embodiment of the present invention with the implant after the expansive deformation.

Referring to FIGS. 1 and 2, an implant 20 according to one embodiment is configured to be placed in a living body 120, is expansively deformable and contractively deformable, and has a first layer 30 (refer also to FIG. 9A) which is formed from a porous membrane and partitions a filling unit 31 filled with a filling material m used to maintain an expanded state of the implant 20, a second layer 40 that is formed from a fluid-impermeable membrane and is arranged to cover the first layer 30, and an introduction port 50b that communicates with the filling unit 31 to introduce the filling material m into the filling unit 31. An introduction region 41 into which a fluid permeating the first layer 30 as the filling material m is introduced into the filling unit 31 is introduced is partitioned between the first layer 30 and the second layer 40 (refer also to FIG. 9B). When the implant 20 is in use, a filling member 80 that is used to send the filling material into the implant 20 is used with the implant 20. An implant assembly 10 is configured to include the implant 20 and the filling member 80.

In this embodiment, the implant and the implant assembly can be applied to a spacer for spacing between spinous processes, a purpose of which is lumbar spinal canal stenosis (lumbar spinal stenosis) treatment.

Figure 5A:
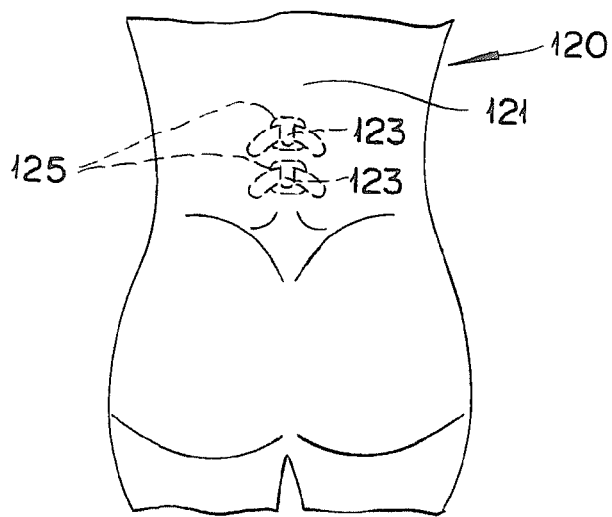
FIGS. 5A-5C are views illustrating spinous processes of the living body to which the implant is applied.
Figure 5B:
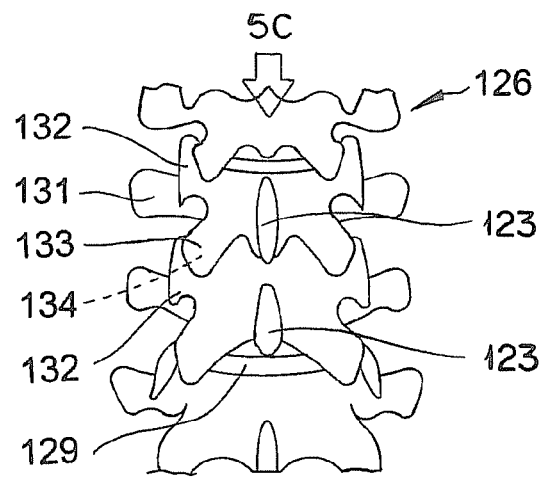
Figure 5C:
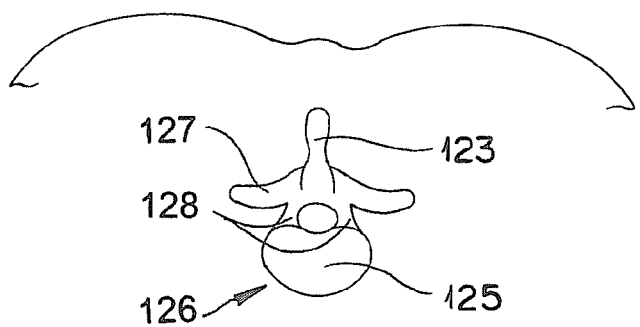

The lumbar spinal canal stenosis will be described briefly. Referring to FIGS. 5A to 5C, in a lumbar vertebra 126 that is positioned on a back 121 of the living body 120, a vertebral body 125 as a front half and a lamina of vertebral arch 127 as a rear half are interconnected via a pedicle of vertebral arch 128. Processes such as spinous processes 123, transverse processes 131, superior articular processes 132, and inferior articular processes 133 are formed in the lamina of vertebral arch 127. The vertebral body 125 normally has a shape slightly curved toward a front side of the living body 120. Adjacent lumbar vertebrae are interconnected via an intervertebral disk (disci intervertebrales) 129, and a certain lumbar vertebra and a lumbar vertebra that is adjacent to the lumbar vertebra are prevented from getting out of alignment with each other by the intervertebral disk 129 and a facet joint 134 between the superior articular process 132 and the inferior articular process 133. However, in a case where a load is repeatedly exerted on the lumbar vertebra 126 due to sports or the like to cause a fatigue fracture, there would result lumbar spondylolysis in which the lumbar vertebra 126 is separated at a part of the pedicle of vertebral arch 128 or lumbar degenerated spondylolisthesis in which it becomes difficult to fix the lumbar vertebra 126 positioned on an upper side due to deformation of the facet joint 134 and degeneration of the intervertebral disk 129 and a slip-off is thereby caused. Further, a severe slip of lumbar vertebra 126 may cause stenosis of the vertebral canal, possibly leading to intermittent claudication, which is a symptom of lumbar spinal canal stenosis. The implant 20 according to the embodiment is used as the spacer for spacing between the spinous processes 123, and can be used to treat the various above-described diseases relating to the lumbar vertebra 126 in a minimally invasive manner and without performing a major surgical procedure.

Figure 7A:
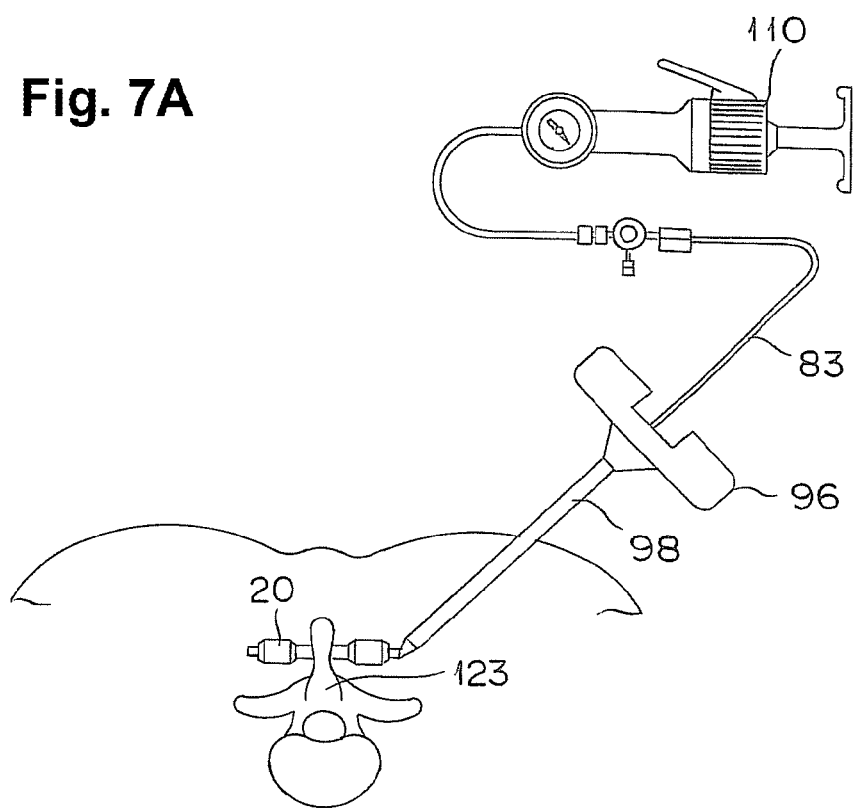
FIGS. 7A and 7B are views illustrating the operation that is performed to place the implant into the living body.
Figure 7B:
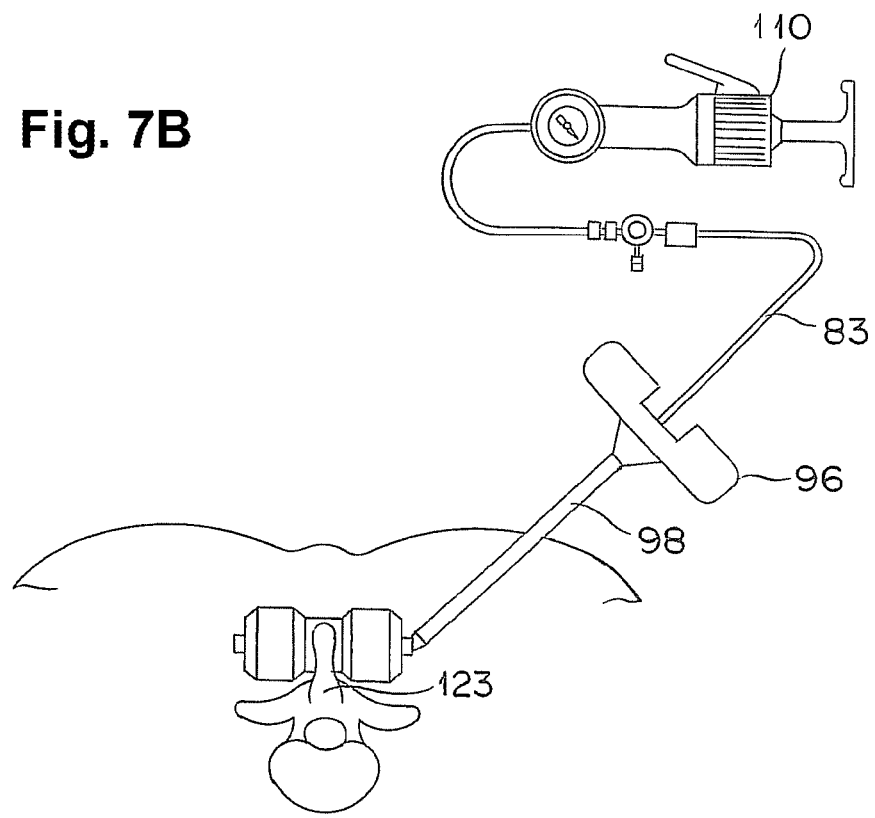

The implant 20 is introduced into the living body 120 in a state before an expansive deformation (refer to FIGS. 1 and 7A), is expansively deformed after being positioned at a placement position in the vicinity of the spinous process 123, and is placed in the expansively deformed state (refer to FIGS. 2 and 7B).

A body section 21 that extends in a longitudinal direction and wide sections 23 that have a greater width than the body section 21 are formed in the implant 20 after the expansive deformation. The body section 21 is formed at a central part of the implant 20, and the wide sections 23 are formed at both end sections of the implant 20 in such a manner that the body section 21 is pinched therebetween. The implant 20 after the expansive deformation has a dumbbell-like (substantially H-like) external shape. A gap between the adjacent spinous processes 123 is maintained in the body section 21 of the implant 20, and misalignment of the implant 20 after the placement is prevented as the spinous processes 123 are pinched by the wide sections 23 positioned at both of the end sections of the implant 20. The shape of the implant 20 before and after an expansion can be appropriately changed if a function as the spacer can be achieved by supporting bones in the living body or holding a gap between the bones with the expansively deformed implant.

The expansion of the implant 20 can be performed by filling the filling unit 31 of the implant 20 with various filling materials such as solids, fluids (gas, liquid, and gel), and the like, and materials of the filling material are not particularly limited. However, in order to maintain the expanded state over a long period of time, it is preferable that the filling material be a solid or a hardening material being fluid at the time of the introduction into the filling unit 31 and hardening after the introduction (hereinafter simply referred to as "hardening material").

Examples of the solids that are used as the filling material include a solid such as metal (such as a super elastic wire and a coil), a granular polymer, and granular ceramic. After the introduction into the implant 20, a state where the implant 20 is placed is maintained without being damaged by a body motion, and thus the function as the spacer between the spinous processes 123 can be achieved over a long period of time in a state where the implant 20 is expansively deformed.

Preferably, the hardening material has at least one of the following characteristics: (a) to be safe to a patient; (b) to cause little or no damage to tissues; (c) to harden at a temperature (approximately 35° C. to 42° C.) close to the body temperature of the patient; (d) to be free of contraction or expansion and be capable of maintaining the shape upon hardening; (e) to harden within one to 60 minutes, preferably five to 30 minutes, and more preferably 10 minutes, after the injection; (f) to allow use of water, a buffer solution, physiological saline, a contrast agent, or oils and fats such as olive oil and castor oil, as a solvent therefor.

Specific examples of the hardening material include (g) a two-part type crosslinking polymer, (h) a hot melt adhesive, (i) a urethane elastomer, (j) a photo-curing resin, (k) an acrylic resin, (l) a bone cement, (m) a solution which is crystallized in response to an external stimulus.

Preferably, the two-part type crosslinking polymer of (g) above is a combination of an aromatic diepoxide resin or an aliphatic diepoxide resin with an amine compound.

Examples of the hot melt adhesive of (h) above include a combination of a material capable of being hardened by reaction with water with water, or adhesives based on ethylene-vinyl acetate copolymer (EVA), polyolefin (PO), polyamide (PA), synthetic rubber (SR), acryl (ACR), and polyurethane (PUR; moisture-hardening type).

Preferably, the urethane elastomer of (i) above is a polymer which is derived from a polyol and an aromatic polyisocyanate.

Examples of the photo-polymerizable monomer of (j) above include acrylate, methacrylate, and ethylenically unsaturated carboxylic acid. A polymerization accelerator, a crosslinking agent, a photo-polymerization initiator or the like can be used as required.

Examples of the acrylic resin of (k) above include those obtained by polymerization, according to known methods, of such a monomer as methyl(meth)acrylate, ethyl(meth)acrylate, butyl(meth)acrylate, n-hexyl(meth)acrylate, cyclohexyl (meth)acrylate, 2-ethylhexyal(meth)acrylate, n-octyl(meth) acrylate, nonyl(meth)acrylate, decyl(meth)acrylate, (meth) acrylic acid, glycidyl(meth)acrylate, vinyl acetate, styrene, a-methylstyrene, (meth)acrylamide, and (meth)acrylonitrile.

The bone cement of (l) above is prepared, for example, by mixing a powder of polymethyl methacrylate, a methyl methacrylate-styrene copolymer, benzoyl peroxide, barium sulfate or the like with a solvent such as methyl methacrylate, N,N-dimethyl-p-toluidine, hydroquinone, and the like. Alternatively, a dental cement that is hardened through an acid-base reaction between zinc oxide and phosphoric acid, an organic-inorganic composite in which a solvent is mixed with sodium alginate, sodium phosphate, calcium chloride and the like to prepare sodium alginate that is an organic material and calcium phosphate that is an inorganic material are prepared, and the like can also be used.

Examples of the solution which is crystallized in response to an external stimulus of (m) above include an aqueous solution prepared by dissolving sodium acetate, sodium chloride or the like. Examples of the external stimulus include a physical shock, heat, light, electricity, and an ultrasonic wave.

By using the hardening material being fluid at the time of the introduction and hardening after the introduction as the filling material, the implant 20 can function as the spacer between the spinous processes 123 over a long period of time in a state of being expansively deformed as in a case where the solid is used as the filling material.

In a case where the solid or the hardening material is used as the filling material, the porous membrane not permeated by these filling materials is used in the first layer 30 of the implant 20. The porous membrane that is used in the first layer 30 may be any (membrane) that is not permeated by the hardening material being fluid at the time of the introduction and hardening after the introduction, and examples thereof include a fibrous porous membrane such as woven fabric, knitted fabric, non-woven fabric, and a paper material and a dense membrane such as a non-fibrous porous membrane and a polymer sheet. Examples of materials of the porous membrane include natural fibers such as cellulose fiber, cotton, linter, kapok, flax, hemp, ramie, silk, and wool, chemical fibers such as polyolefins such as nylon (polyamide), tetrone, rayon, cupra, acetate, vinylon, acryl, polyethylene, and polypropylene, polyesters such as polyethylene terephthalate, polybutylene terephthalate, polyoxyethylene terephthalate, polyethylene naphthalate, polycyclohexane dimethylene terephthalate, and polypropylene terephthalate, cellulose-based polymers such as cellulose acetate and cellulose nitrate, fluorine-containing polymers such as polytetrafluoroethylene (PTFE, ePTFE) and tetrafluoroethylene-ethylene copolymer, metal fibers such as SUS wire, copper wire (plated copper wire), tungsten wire, boron wire, shape memory-super elastic alloy (NiTi) wire, and various surface-treated-coat wires of these wire materials, inorganic fibers such as alumina fiber, silicon carbide fiber, and carbon fiber or a combination (mixed yarn) of at least two thereof. The same material as the impermeable membrane used in the second layer 40, which will be described later, is used in the porous membrane of the first layer 30, and the above-described characteristics as the porous membrane can be provided by forming a fine hole in the above-described impermeable membrane by a needle tip or laser.

A gas-impermeable membrane is used in the second layer 40. Preferably, various polymer materials (particularly thermoplastic resin) are used in the impermeable layer used in the second layer 40, and a material that has flexibility as a whole can be used. Examples of the constituting materials include polyesters such as polyethylene terephthalate and polybutylene terephthalate or polyester elastomer containing the above, olefin-based resins such as polyethylene and polypropylene or what is crosslinked thereon (particularly what is crosslinked through electron beam irradiation), polyamide-based resins such as nylon 11, nylon 12, nylon 610 or polyamide elastomer containing the above, polyurethane, polytetrafluoroethylene (PTFE, ePTFE), and ethylene-vinyl acetate copolymer containing the above or what is crosslinked thereon, butadiene-based rubbers such as silicone rubber (Q), natural rubber (NR), isoprene rubber (IR), butadiene rubber (BR, 1, 2-BR), and styrene-butadiene rubber (SBR), diene-based special rubbers such as chloroprene rubber (CR) and butadiene acrylonitrile rubber (NBR), olefin-based rubbers such as butyl rubber (IIR), ethylene-propylene rubber (EPM, EPDM), acrylic rubber (ACM, ANM), and halogenated butyl rubber (X-IIR), urethane-based rubbers such as urethane rubber (AU, EU), ether-based rubbers such as hydrin rubber (CO, ECO, GCO, EGCO), polysulfide-based rubbers such as polysulfide rubber (T), various rubbers such as fluororubber (FKM, FZ) and chlorinated polyethylene (CM), and various thermoplastic elastomers based on styrene, polyolefin, polyvinyl chloride, polyurethane, polyester, polyamide, polybutadiene, trans-polyisoprene, fluororubber, chlorinated polyethylene and the like, one or more of which can be used in a mix.

It is preferable that a fiber material is used in at least one of the first layer 30 or the second layer 40. Examples of the fiber material include natural fibers such as cellulose fiber, cotton, linter, kapok, flax, hemp, ramie, silk, and wool, chemical fibers such as polyolefins such as nylon (polyamide), tetrone, rayon, cupra, acetate, vinylon, acryl, polyethylene, and polypropylene, polyesters such as polyethylene terephthalate, polybutylene terephthalate, polyoxyethylene terephthalate, polyethylene naphthalate, polycyclohexane dimethylene terephthalate, and polypropylene terephthalate, cellulose-based polymers such as cellulose acetate and cellulose nitrate, fluorine-containing polymers such as polytetrafluoroethylene (PTFE, ePTFE) and tetrafluoroethylene-ethylene copolymer, metal fibers such as SUS wire, copper wire (plated copper wire), tungsten wire, boron wire, shape memory-super elastic alloy (NiTi) wire, and various surface-treated-coat wires of these wire materials, inorganic fibers such as alumina fiber, silicon carbide fiber, and carbon fiber or a combination (mixed yarn) of at least two thereof.

By causing the first layer 30 and the second layer 40 to contain the fiber material, the permeability of the first layer 30 and the impermeability of the second layer 40 can be maintained while the strength of each can be improved.

In a case where the fiber material is used, it is preferable that a net structure 49 be formed by the fiber material. The strength of each of the layers can be further improved by forming the net structure 49 in a part of the layer or the entire layer. In the implant 20, the net structure 49 having a grid shape is formed of the fiber material and is disposed to cover an entire outer surface of the second layer 40 (refer to FIG. 1).

The use of the fiber material and the formation of the net structure 49 by the fiber material can be omitted, and the net structure can be disposed on either one of the layers or the net structure can be partially disposed in each of the layers. Also, the shape of the net and a gap in the net are not limited to what is shown but can be appropriately changed.

The second layer 40 is coated with a water-swellable polymer material. When the implant 20 is introduced into the living body 120, the water-swellable polymer material coating the second layer 40 swells by reacting to moisture of the filling material or a body fluid in the living body 120, and thus the amount of deformation of the implant 20 before and after the expansive deformation increases. Accordingly, by using a water-swellable polymer, an adjustment of the amount of the deformation can be performed before and after the expansive deformation. Also, a movement of the spinous processes by the implant 20 can be buffered and a fracture can be prevented. In addition, in a case where a hardening material causing heat generation in the filling material is used, the heat can be insulated such that burning of the living body is prevented.

Preferable examples of the water-swellable polymer material include what is in contact with water at approximately normal temperature to body temperature and swells twice to 1,000 times its own weight within 10 minutes, and various materials known as high-absorbent resins can be used. The examples thereof include acrylate-based starch graft product containing hydrolyzates such as starch acrylonitrile, starch acrylate, starch acrylamide, and starch sodium acrylate, pregelatinized starch, polyvinyl alcohol-based resin, polyacrylate-based resin, acrylic acid-vinyl alcohol-based polymer, polyethylene oxide-based polymer, cellulose-based polymer, crosslinking N-vinyl carboxylic acid amide resin, vinyl acetate-acrylic acid salt-based resin, isobutylene-maleic acid-based resin, poly N-vinyl acetamide-based resin, polyether-based urethane resin, polyester-based urethane resin, polyester-polyether-based urethane resin, polycarbonate-based urethane resin, acrylic polymer, and the like.

Figure 3A:
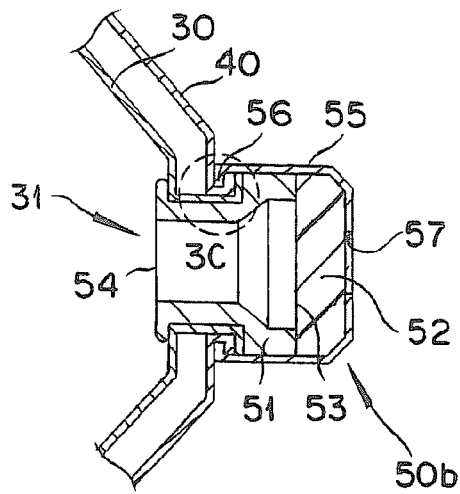
FIGS. 3A-3C are partially enlarged views illustrating an introduction port of the implant and a filling member that sends a filling material into the implant.
Figure 3B:
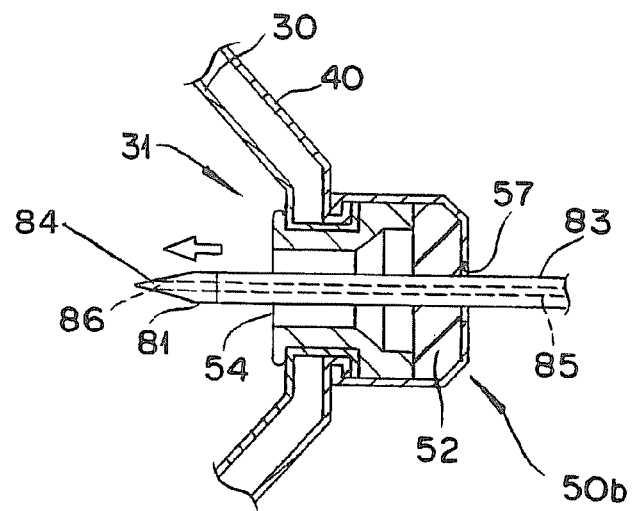

Referring to FIGS. 3A and 3B, the introduction port 50b disposed in the implant 20 has an inner pipe member 51 that has an open end 54 which communicates with the filling unit 31 partitioned by the first layer 30, a sealing section 52 that covers an open end 53 positioned on the opposite side to the open end 54 of the inner pipe member 51, and an outer pipe member 55 that can be attached to and detached from the inner pipe member 51.

The inner pipe member 51 and the outer pipe member 55 are formed from a metallic material and a resin material.

Examples of the metallic material include one or more of various living body-compatible metallic materials such as SUS, titanium, magnesium, chromium, cobalt, nickel, aluminum, gold, silver, copper, iron, iridium, tantalum molybdenum, zirconium, chromium/titanium alloy, chromium/nickel alloy, chromium/cobalt alloy, cobalt/titanium alloy, nickel/titanium alloys such as nitinol, platinum, and platinum-tungsten alloy.

Examples of the resin material include one or more various living body-compatible metallic materials such as polyether ether ketone (PEEK), polyether ketone ketone (PEKK), polycarbonate urethane (PCU), reinforced polyphenylene (SRP), carbon or glass fiber reinforced polymer, ABS, polycarbonate, polyethylene, ultra-high molecular weight polyethylene (UHMWPE), nylon, polymer composite, acetal, polyester, polypropylene, polytetrafluoroethylene (PTFE, ePTFE) and other living body-compatible polymers, poly-L-lactic acid (PLLA), polylactic acid (PLA), and polyglycolic acid (PGA).

Figure 3C:
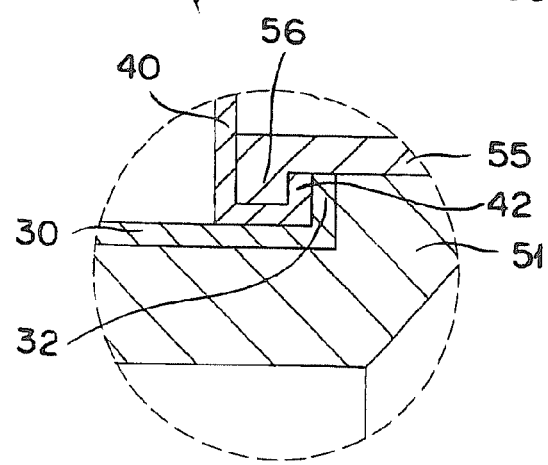

Referring to FIG. 3C, an end section 32 of the first layer 30 and an end section 42 of the second layer 40 are connected with each other in a state of being pinched by a predetermined part on an outer surface of the inner pipe member 51 and a predetermined part on an inner surface of the outer pipe member 55. The first layer 30 is attached to the inner pipe member 51 by, for example, fitting or an adhesive, heat seal, and the like. Also, the adhesive, heat seal, and the like are used in attachment between the second layer 40 and the first layer 30.

An opening section 57 is disposed in the outer pipe member 55 so as to introduce a distal end section 81 of the filling member 80. In the attachment between the inner pipe member 51 and the outer pipe member 55, a form of connection in which both of the members 51 and 55 are mechanically connected is used. For example, as shown in FIG. 3C, an engagement pin 56 that can be engaged with the inner pipe member 51 is disposed in the outer pipe member 55. The inner pipe member 51 and the outer pipe member 55 are connected with each other by the engagement pin 56. In this manner, the first layer 30 and the second layer 40 may be connected by the engagement between the inner pipe member 51 and the outer pipe member 55 without being attached by, for example, the adhesive, heat seal, and the like.

The sealing section 52 is formed from an elastically deformable elastic material. Examples of the elastic material include various rubber materials such as natural rubber, isoprene rubber, butadiene rubber, styrene-butadiene rubber, nitrile rubber, chloroprene rubber, butyl rubber, acryl rubber, ethylene-propylene rubber, hydrin rubber, urethane rubber, silicone rubber, and fluororubber, and various thermoplastic elastomers based on styrene, polyolefin, polyvinyl chloride, polyurethane, polyester, polyamide, polybutadiene, trans-polyisoprene, fluororubber, chlorinated polyethylene, and the like, one or more of which can be used in a mix. By using the elastic material, the sealing section 52 can obtain proper elasticity, and thus the sealing section 52 and the inner pipe member 51 and the outer pipe member 55 can be in contact in a liquid-tight manner.

Two introduction ports 50a and 50b are disposed in the implant 20. The introduction port 50a is disposed on a distal end side (left side in FIGS. 1 and 2) in the direction of the introduction into the living body 120, and the introduction port 50b is disposed on a proximal end side (right side in FIGS. 1 and 2) in the direction of the introduction oppositely to the introduction port 50a. Any of the introduction ports 50a and 50b can be used to fill the implant 20 with the filling material.

The number of introduction ports installed and location of installation are not particularly limited insofar as the filling material can be introduced into the filling unit 31. Also, the introduction port 50a and the introduction port 50b can have similar configurations and can have different configurations from each other.

The filling member 80 that is used to send the filling material into the filling unit 31 has the distal end section 81 which is inserted into the filling unit 31 of the implant 20 via the introduction port 50b, an opening section 84 which is disposed in the distal end section 81 to introduce the filling material into the filling unit 31, and a tubular member 83 which has a lumen 85 communicating with the opening section.

Referring to FIGS. 1 to 3, the distal end section 81 of the filling member 80 is formed in a needle shape to be capable of penetrating the sealing section 52 of the introduction port 50b. The distal end section 81 can be formed from a metallic material, a resin material which has predetermined rigidity, and the like.

The tubular member 83 is configured to have a tube in which the lumen 85 is formed. The tube can be formed, for example, from a known resin tube which is in wide use in the medical field and the like.

A connector 87 to which a supply device 110 used to send the filling material is connected is disposed on a proximal end side of the tubular member 83 (refer to FIG. 7A). The connector 87 also has a function as a valve to maintain the lumen 85 of the tubular member 83 in an air-tight and liquid-tight manner inside.

Various fluids are sealed in advance in the lumen 85 of the tubular member 83 before the placement of the implant 20 in the living body 120. In this embodiment, air is sealed. When the implant 20 is expanded, the sealed air passes through the filling unit 31 and also passes through the first layer 30 to be introduced into the introduction region 41.

It is preferable that the volume of the lumen 85 of the tubular member 83 be equal to the volume of the introduction region 41 or be larger than the volume of the introduction region 41. If the lumen 85 is formed to have the volume, the introduction region 41 of the implant 20 can be filled with the fluid (air) that is sealed in advance in the lumen 85 of the tubular member 83 when the implant 20 is expansively deformed. For example, in a case where the volume of the introduction region 41 of the implant 20 is approximately 0.1 to 30 cm$^3$, the volume of the lumen 85 of the tubular member 83 is approximately 0.1 to 300 m$^3$.

An inner lumen 86 that communicates with the lumen 85 of the tubular member 83 is disposed in the distal end section 81 of the filling member 80. The filling material that is sent through the lumen 85 of the tubular member 83 is introduced into the filling unit 31 via the opening section 84 which is disposed in the distal end section 81 of the filling member 80. The shape and installation position of the opening section 84 are not particularly limited insofar as the filling material can be introduced into the filling unit 31 from the opening section 84 in a state where the implant 20 and the filling member 80 are connected with each other. For example, an open hole can be disposed on a side surface of the distal end section 81 such that the hole is used as the opening section.

The connection between the implant 20 and the filling member 80 is performed by pushing the distal end section 81 of the filling member 80 into the sealing section 52 of the introduction port 50b and arranging the opening section 84 which is disposed in the distal end section 81 of the filling member 80 in the filling unit 31 (refer to FIG. 3B). In this manner, preparations for a connection operation through which the implant 20 and the filling member 80 are interconnected and a filling operation performed via the opening section 84 through which the filling unit 31 is filled with the filling material are performed in the same process.

After the connection, an outer circumferential surface of the tubular member 83 is covered by the sealing section 52, and thus a liquid-tight and air-tight state can be maintained between the tubular member 83 and the sealing section 52.

Separation between the implant 20 and the filling member 80 is performed by pulling out the distal end section 81 of the filling member 80 from the filling unit 31. When the distal end section 81 of the filling member 80 is pulled out, the sealing section 52 is elastically deformed and blocks the introduction port 50b. The sealing section 52 has the self-sealing function.

Referring to FIG. 2, a plurality of connection members 70 that connect the first layer 30 and the second layer 40 with each other are disposed in the implant 20. Since the connection members 70 are disposed, relative positions of the first layer 30 and the second layer 40 are positioned. As shown in the drawing, the connection members 70 are arranged, for example, to penetrate the introduction region 41 and connect the first layer 30 and the second layer 40 with each other. The external shape and the like of each of the connection members 70 are not limited and, for example, the shape is formed into a pillar shape such that each of the layers 30 and 40 can be connected and supported at predetermined parts.

The introduction port 50b can be used as the connection member 70 that connects the first layer 30 and the second layer 40 with each other. For example, the introduction port 50b that is disposed on the proximal end side in the direction of the introduction of the implant 20 into the living body 120 is used as a proximal end side connection member 72 that connects the first layer 30 and the second layer 40 with each other.

A body section side connection member 73 that connects the first layer 30 and the second layer 40 with each other in the body section 21 and a wide section side connection member 75 that connects the first layer 30 and the second layer 40 with each other in the wide section 23 are further disposed in the implant 20. During the expansion, it is preferable that the introduction region 41 be formed with a uniform thickness around the filling unit 31, but parts where the body section 21 and the wide section 23 are formed have a large amount of deformation (amount of swelling) before and after the expansion, and thus are likely to be not sufficiently expansively deformed compared to the other parts. When the connection members 70 that connect the first layer 30 and the second layer 40 with each other are disposed in the body section 21 and the wide section 23, the second layer 40 can be expansively deformed following the expansive deformation of the first layer 30. In this manner, the introduction region 41 is formed with a uniform thickness.

It is preferable that the connection members 70 be disposed in pairs such that the first layer 30 and the second layer 40 are respectively connected with each other at opposing positions of the implant 20. In the implant 20, the introduction region 41 can be formed with a uniform thickness at a target position on a central axis of the implant 20 when the connection members 70 are disposed in pairs. To this end, as shown in the drawing, a total of the eight connection members 70 are disposed, one being the proximal end side connection member 72, one being a distal end side connection member 71 that is disposed in a pair with the proximal end side connection member 72, two being the body section side connection members 73, four being the wide section side connection members 75.

The distal end side connection member 71 is configured to have the introduction port 50a that is positioned on the distal end side where the first layer 30 and the second layer 40 are fixed. The distal end side connection member 71 and the proximal end side connection member 72 are arranged on an axis along the direction of the introduction, and thus a misalignment of the first layer 30 and the second layer 40 is effectively prevented during the introduction into the living body 120.

The number and shapes of the connection members 70 are not particularly limited insofar as the relative misalignment between the first layer 30 and the second layer 40 can be prevented. For example, what is formed into a ring shape and extends along and around a longitudinal axis of the implant 20 can be used in the body section side connection member 73 and the wide side connection member 70. Also, only the connection members that have a pillar shape similar to the other connection members and another shape can be used without constituting the connection members 70 by using the introduction port 50b.

Examples of materials constituting the connection members 70 include resin materials and metallic materials.

In a case where a hardening material that generates heat with time after the introduction of the filling material is used, a thermally expandable resin material is used as the resin material. In a case where the thermally expandable resin material is used, the resin material expands due to the heat generated by the hardening material, and thus a proper distance can be maintained between the first layer 30 and the second layer 40. Also, a heat shrinkable resin material can be selected as the resin material. In a case where the heat shrinkable resin material is used, the resin material contracts due to the heat generated by the hardening material, and thus the first layer 30 and the second layer 40 are more firmly fixed and a misalignment between the first layer 30 and the second layer 40 is effectively prevented.

Examples of the thermally expandable material that is used include polyacrylonitrile-based copolymer, polymethacrylonitrile-based copolymer, polyvinylidene chloride-based copolymer, polystyrene or polystyrene-based copolymer, polyolefin, and polyphenylene oxide-based copolymer.

Examples of the thermally shrinkable material that is used include polyethylene, polyolefin, polyvinyl chloride, polyvinylidene fluoride, chlorosulfonated polyethylene, chlorinated polyethylene, ethylene-acrylic acid ester copolymer, fluorinated elastomer, ethylene-propylene rubber, butadiene-acrylonitrile rubber, silicone elastomer, chloro-silicone-based elastomer, urethane elastomer, polyolefin-based elastomer, and heat shrinkable resins such as thermoplastic elastomer in which these elastomers are mixed with vinyl chloride resin.

In a case where the metallic material is used in the connection members 70, the first layer 30 and the second layer 40 can be firmly fixed regardless of the type of the filling material, and thus a misalignment can be appropriately prevented during the introduction of the implant 20 and the expansive deformation of the implant 20.

Examples of the metallic material include one or more various living body-compatible metallic materials such as SUS, titanium, magnesium, chromium, cobalt, nickel, aluminum, gold, silver, copper, iron, iridium, tantalum molybdenum, zirconium, chromium/titanium alloy, chromium/nickel alloy, chromium/cobalt alloy, cobalt/titanium alloy, nickel/titanium alloys such as nitinol, platinum, and platinum-tungsten alloy.

FIGS. 4A and 4B show a puncture tool 90 that is used to introduce the implant 20 into the living body 120. The puncture tool 90 has an inner needle 91 that is punctured into the living body 120, and an outer needle 96 that is used in assembly with the inner needle 91. The inner needle 91 has a main body section 92 where a needle section 93 is disposed at a tip. The outer needle 96 has a grip section 97, and a cylindrical section 98 into and from which the main body section 92 of the inner needle 91 can be inserted and removed.

The inner needle 91 and the outer needle 96 are fixed to each other in a state where the main body section 92 of the inner needle 91 is inserted into the cylindrical section 98 of the outer needle 96 (refer to FIG. 4B). The fixing is performed by screwing in a threaded section 99 which is formed in the main body section 92 of the inner needle 91 and the cylindrical section 98 of the outer needle 96. When the introduction of the implant 20 is performed, the inner needle 91 and the outer needle 96 are in an assembled state and the needle section 93 of the inner needle 91 is punctured into the living body 120 (refer to FIG. 6B). In this state, the inner needle 91 is separated from the outer needle 96, the main body section 92 of the inner needle 91 is pulled out of the cylindrical section 98, and the inner needle 91 is removed from the living body 120. The implant 20 is introduced into a predetermined part of the living body 120 by using the cylindrical section 98 of the outer needle 96.

A procedure of the placement of the implant 20 and an effect of the implant 20 according to this embodiment will be described.

Figure 6A:
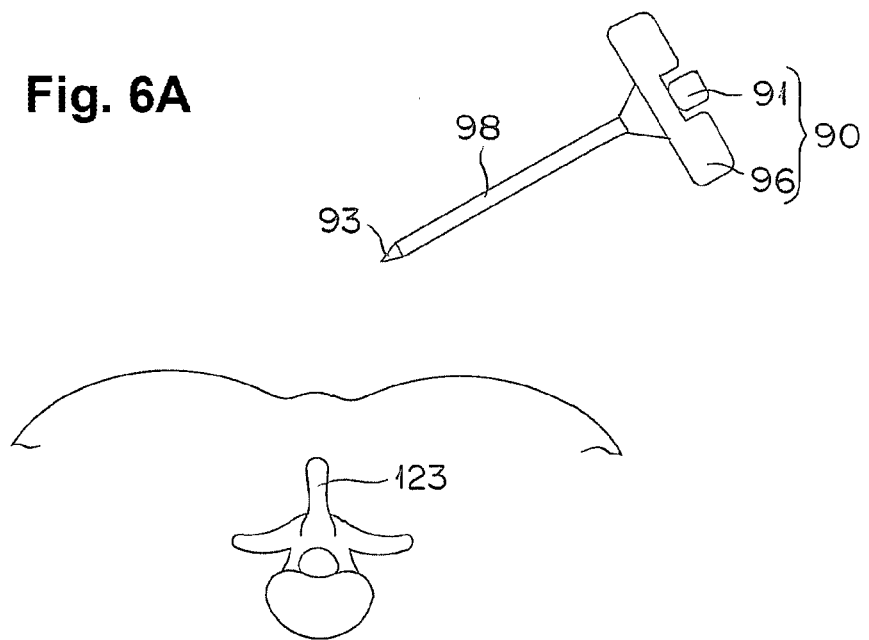
FIGS. 6A and 6B are views illustrating an operation that is performed to place the implant into the living body.

Referring to FIG. 6A, the puncture tool 90 in which the inner needle 91 and the outer needle 96 are assembled with each other is prepared.

Figure 6B:
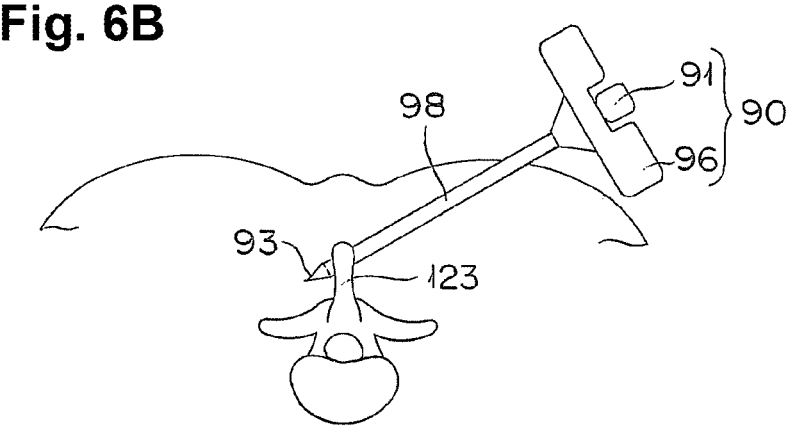

Referring to FIG. 6B, the puncture tool 90 is introduced into the living body 120. In this case, a distal end section of the inner needle 91 and a distal end section of the outer needle 96 are positioned between the spinous processes. Then, the inner needle 91 is separated and withdrawn from the outer needle 96.

Referring to FIG. 7A, the implant 20 before the expansive deformation is introduced into the living body 120 through the cylindrical section 98 of the inner needle 91. The implant 20 is extracted from a tip of the outer needle 96 and is positioned between the spinous processes 123. The introduction of the implant 20 can be performed through manual push by a practitioner or can be performed by using a pushing member such as a bar and a tube.

Referring to FIG. 7B, the filling material m is introduced into the filling unit 31 of the implant 20 and the implant 20 is expansively deformed.

In a case where the hardening material and the fluid are used as the filling material m, the supply device 110 can be used to pump these filling materials m. A known indeflator and the like can be used as the supply device 110. Also, in a case where the supply device 110 is used, connection with the supply device 110 is performed via the connector 87 of the filling member 80. In a case where a solid is used as the filling material m, the introduction can be performed by flowing or pushing the filling material m into the cylindrical section 98 of the outer needle 96 without using the supply device 110.

Before performing the filling operation to fill the filling material m, the filling unit 31 can be filled with a contrast agent. The implant 20 is preliminary expanded by performing such an operation, and thus an expansion operation by the filling material m can be performed smoothly. Also, an introduction position and a final expansion shape of the implant 20 can be ensured by performing X-ray transillumination in a state where the contrast agent is filled. The contrast agent is suctioned by the indeflator and the like before the introduction of the filling material m and is discharged from the filling unit 31.

FIG. 9 schematically shows how the fluid is introduced into the introduction region 41 during the introduction of the filling material m into the filling unit 31.

Figure 9A:
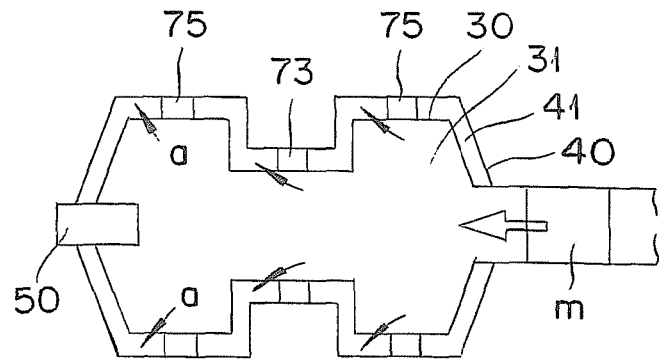
FIGS. 9A and 9B are views illustrating an effect of the implant.

Referring to FIG. 9A, air a that is sealed in the lumen 85 is introduced ahead of the filling material m into the filling unit 31 of the implant 20 when the implant 20 is expanded in the living body 120 and the filling material m is sent into the tubular member 83. The expansive deformation of the implant 20 is initiated by the introduction of the air a into the filling unit 31. When the filling material m begins to be introduced into the filling unit 31, the air a introduced into the filling unit 31 permeates the first layer 30 and is introduced into the introduction region 41.

Then, the filling unit 31 is filled with the filling material m and the introduction region 41 is filled with the air a. The implant 20 is expansively deformed until reaching the substantially H-like final expansion shape placed in the living body 120.

Figure 9B:
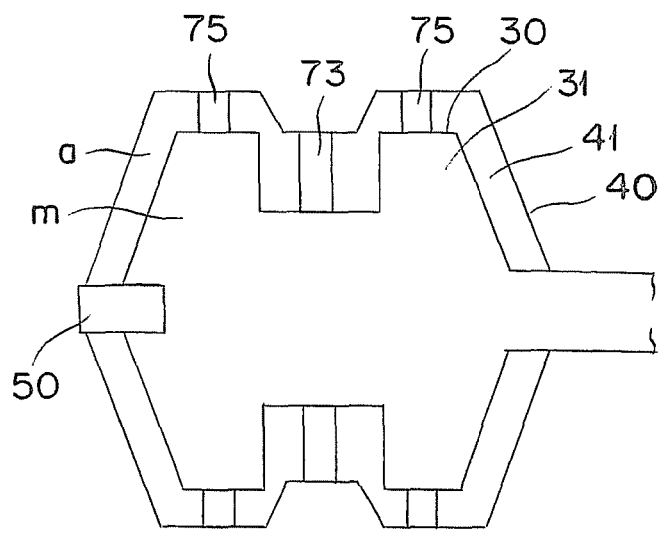

Referring to FIG. 9B, the expansion shape of the implant 20 is maintained over a long period of time as the filling unit 31 is filled with the filling material m. The introduction region 41 is arranged between the filling unit 31 that is filled with the filling material m and the spinous processes 123 that are present around the implant 20, and functions as a buffer layer which reduces a load applied to the spinous processes 123. Also, in a case where a hardening material that generates heat during hardening is used as the filling material m, the filling unit 31 functions as a heat insulating layer to suppress heat transmission toward the implant 20.

Figure 8A:
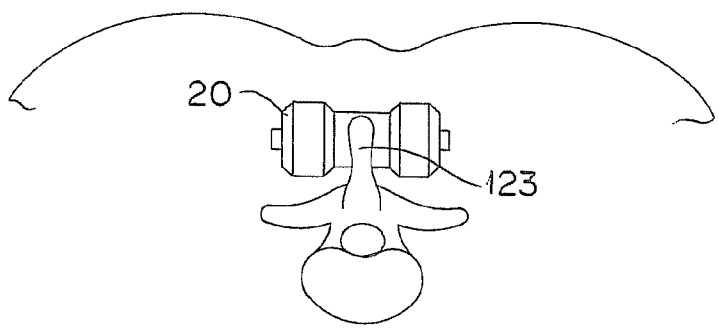
FIGS. 8A and 8B are views showing the implant that is placed between the spinous processes.
Figure 8B:
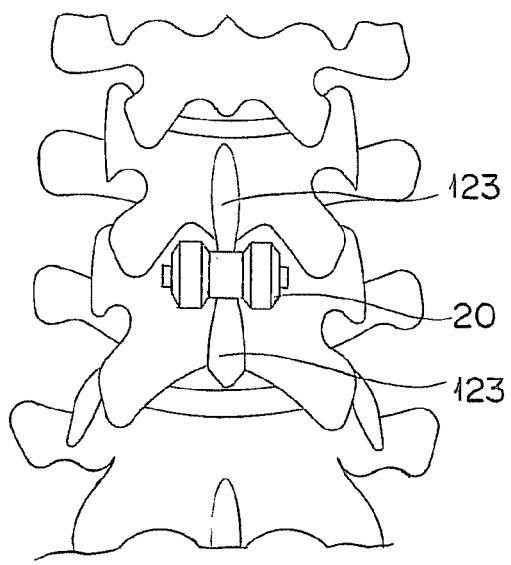

Referring to FIG. 8, the filling member 80 is separated from the implant 20. Then, the outer needle 96 of a puncture member is removed from the living body 120. The implant 20 is placed between the spinous processes 123 and is used as the spacer for spacing between the spinous processes 123.

As described above, according to this embodiment, the gas that functions as a buffer material can be held in the introduction region 41 which is partitioned to cover the filling unit 31, and thus the load onto the living body can be reduced regardless of the type of the filling material used to maintain the expanded state of the implant in use. Accordingly, in a procedure during which the implant 20 is placed into the living body 120, various materials can be widely applied to the filling material m, and thus the filling material m of an optimal material can be used depending on various procedures and application sites in the living body. Moreover, the fluid present in the filling unit 31 can be introduced into the introduction region 41 with the introduction of the filling material m into the filling unit 31, and thus an introduction path to introduce the fluid into the introduction region 41 does not have to be disposed in addition to an introduction path to introduce the filling material m into the filling unit 31. Accordingly, the introduction of the implant 20 into the living body 120 can be performed in a minimally invasive manner.

Also, the solid or the hardening material being fluid at the time of the introduction into the filling unit 31 and hardening after the introduction is used as the filling material m and the porous membrane not permeated by the filling material m is used in the first layer 30, and thus the expansion shape of the implant 20 can be maintained over a long period of time by the filling material m with which the filling unit 31 is filled.

Also, at least either one of the material constituting the first layer 30 and the material constituting the second layer 40 has the fiber material, and thus the strength of the first layer 30 and the second layer 40 can be improved.

Also, by coating the second layer 40 with the water-swellable polymer material, the amount of volume change of the implant 20 can be adjusted before and after the expansive deformation. Also, the movement of the spinous processes by the implant 20 can be buffered and the fracture can be prevented. In addition, in a case where the hardening material causing the heat generation in the filling material is used, the heat can be insulated such that burning of the living body is prevented.

Also, the relative positions of the first layer 30 and the second layer 40 can be positioned by connecting the first layer 30 and the second layer 40 with each other, and a misalignment can be prevented during the introduction into the living body 120.

Also, since the introduction port 50b also has the function as the connection member 70 which connects the first layer 30 and the second layer 40 with each other, the number of components required to connect the first layer 30 and the second layer 40 with each other can be reduced.

Also, since the body section side connection member 73 and the wide section side connection member 75 that connect the first layer 30 and the second layer 40 with each other are disposed in the body section 21 and the wide section 23 of the implant 20, the second layer 40 can be expansively deformed following the expansive deformation of the first layer 30, and the introduction region 41 can be formed with a uniform thickness around the filling unit 31.

Also, since the connection members 70 are disposed in pairs such that the first layer 30 and the second layer 40 are respectively connected with each other at the opposing positions of the implant 20, the introduction region 41 can be formed with a uniform thickness at the target position on the central axis of the implant 20.

Also, by connecting the implant 20 and the filling member 80 with each other and arranging the opening section 84 which is disposed in the filling member 80 and is used to introduce the filling material in the filling unit 31, the preparations for the connection operation through which the implant 20 and the filling member 80 are interconnected and the filling operation performed via the opening section 84 through which the filling unit 31 is filled with the filling material are performed in the same process, and thus the procedure through which the implant 20 is placed in the living body can be simplified.

Also, since the volume of the lumen 85 of the tubular member 83 of the filling member 80 is equal to the volume of the introduction region 41 or is larger than the volume of the introduction region 41, the introduction region 41 can be filled with the fluid with the introduction of the filling material m into the filling unit 31.

(Modification Example of Implant)

In the modification example, a gel- and liquid-impermeable but gas-permeable porous membrane is used in the second layer 40 partitioning the introduction region 41. In this point, the modification example is different from the above-described embodiment in that the fluid-impermeable membrane is used in the second layer. Hereinafter, another embodiment will be described. The same reference numerals are used to designate the same members as in the above-described embodiment and redundant descriptions thereof are omitted.

In the above-described embodiment, the gas that is introduced into the introduction region 41 functions as the buffer material. The liquid and the gel, for example, can be used as the fluid that is introduced into the introduction region 41. A buffering function and an insulation function of the introduction region 41 can be improved by introducing the liquid and the gel instead of the gas. However, there is a case where a very small amount of gas (air and the like) that is sealed in the implant 20 during the manufacturing remains in the filling unit 31 and the introduction region 41. When such gas is mixed with the liquid and the gel that is introduced into the introduction region 41, the implant 20 may be collapsed or damaged at a mixing part. As such, the gas-permeable porous membrane is used in the second layer 40 of this modification example.

The porous membrane used in the second layer 40 has the same material as the first layer 30 that has been described in the above-described embodiment. For example, the permeation of the liquid and the gel can be limited and the permeation of the gas can be allowed by adjusting the diameter of the hole formed in the porous membrane.

Examples of the liquid that is introduced into the introduction region 41 include water, the contrast agent, and the like. Examples of the gel include hydrophilic gel, hyaluronic acid gel, and the like. In addition, the liquid and the gel can be introduced into the introduction region 41 in combination, and only either one thereof can be introduced into the introduction region 41.

FIGS. 10 and 11 are views illustrating an operation of this modification example.

Figure 10A:
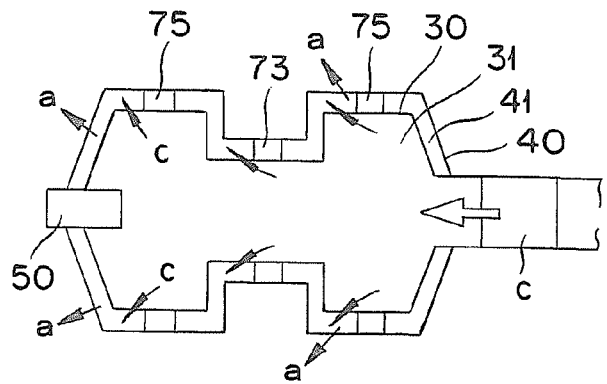
FIGS. 10A and 10B are views illustrating an effect of the implant according to a modification example.

Referring to FIG. 10A, a contrast agent c is sealed in advance, instead of the air a, into the lumen 85 of the tubular member 83. When the contrast agent c is introduced into the filling unit 31, the contrast agent c permeates the first layer 30 and is introduced into the introduction region 41. In this case, the air that remains in the filling unit 31 and the introduction region 41 permeates the second layer 40 to be discharged from the implant 20. The introduction of the contrast agent c can be performed by the indeflator and the like.

Figure 10B:
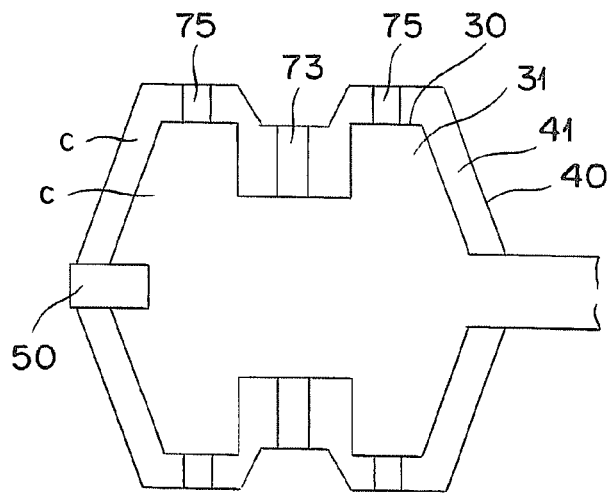

Referring to FIG. 10B, the filling unit 31 and the introduction region 41 are filled with the contrast agent c by continuing the filling of the contrast agent c. The implant 20 is expanded until reaching the substantially H-like final expansion shape. In this case, a surrounding tissue around the spinous processes 123 is pushed to be widened. After the introduction of the contrast agent c, the introduction position and the final expansion shape of the implant 20 can be ensured by performing X-ray transillumination.

Then, the contrast agent c is discharged from the filling unit 31 of the implant 20 by suctioning the contrast agent c filled in the implant 20. The discharge of the contrast agent c can be performed by the indeflator and the like that is used to introduce the contrast agent c. The implant 20 is deformed to be a contraction state before the expansive deformation by discharging the contrast agent c. During this operation, a proper amount of the contrast agent remains in the filling unit 41 such that the contrast agent can function as the buffer material as it is.

Figure 11A:
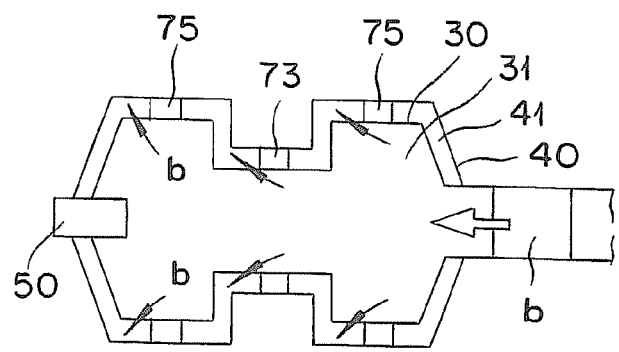
FIGS. 11A and 11B are views illustrating the effect of the implant according to the modification example.

Referring to FIG. 11A, the liquid and the gel (referred to as an introduction medium b in the drawing) are introduced into the filling unit 31 of the implant 20.

Figure 11B:
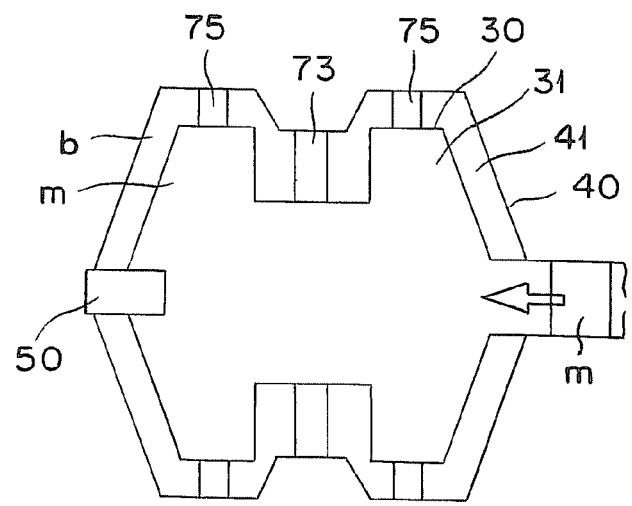

Referring to FIG. 11B, the implant 20 is filled with the filling material m. The gel and the liquid that is introduced into the filling unit 31 ahead of the filling material m permeate the first layer 30 and are introduced into the introduction region 41. The implant 20 is expanded by the introduction of the filling material m until reaching the substantially H-like expansion shape.

In this manner, according to this modification example, the liquid- and gel-impermeable but gas-permeable porous membrane is used in the second layer 40, and thus remaining of the gas in the introduction region 41 can be prevented and the gel and the liquid which functions as the buffer material can be appropriately held in the introduction region 41.

In the description of the modification example, the process of preliminary expansion of the implant 20 using the contrast agent has been described, but the process can be omitted.

(Shape Example of Implant)

The external shape of the implant 20 is not limited to the substantially H shape shown in each of the above-described embodiments, but can be appropriately changed depending on parts of the living body 120 where the implant 20 is placed and applications thereof.

Figure 12A:
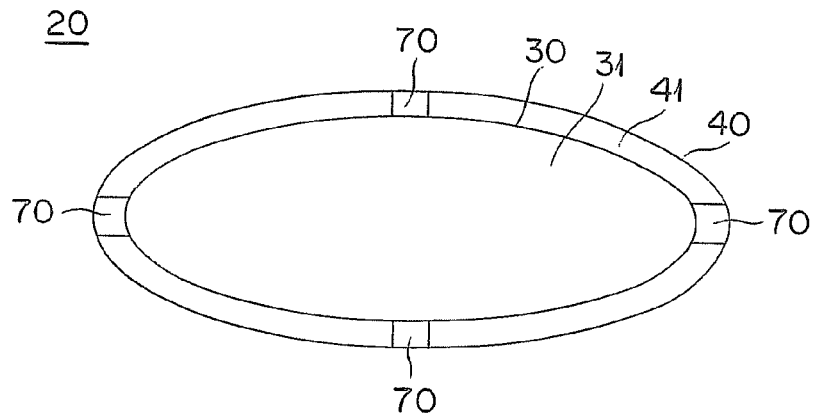
FIGS. 12A to 12C are simplified views showing shape examples of the implant.

For example, as shown in FIG. 12A, the external shape of the implant 20 can be formed into an elliptical shape. In a case where the implant 20 has an elliptical shape, it is preferable that a set of connection members 70 be installed on a long axis and an additional set of the connection members 70 be installed on a short axis such that a proper distance can be maintained between the first layer 30 and the second layer 40.

Figure 12B:
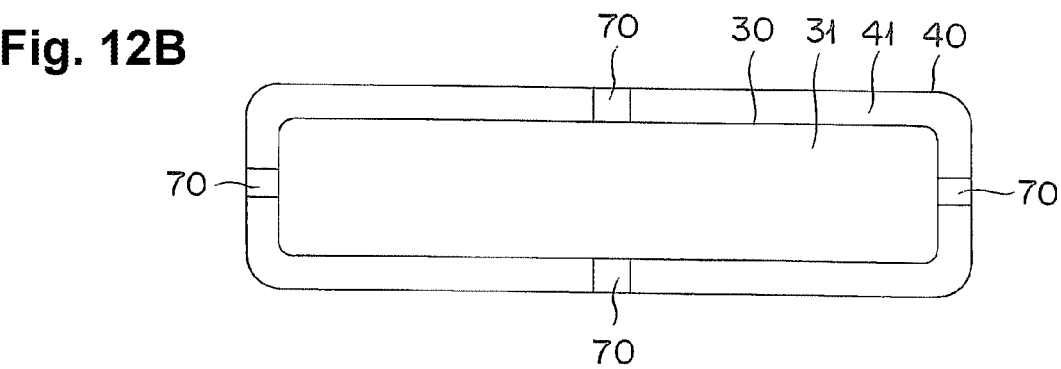

Also, as shown in FIG. 12B, the external shape of the implant 20 can be formed into a substantially rectangular shape from which corner sections are removed. In a case where the implant 20 is formed into such an external shape, it is preferable that a set of the connection members 70 be installed at the center of a short side and an additional set of connection members 70 be installed at the center of a long side such that a proper distance can be maintained between the first layer 30 and the second layer 40.

Figure 12C:
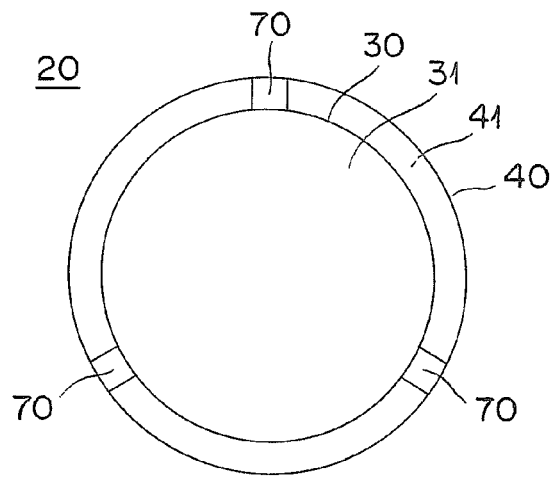

Also, as shown in FIG. 12C, the external shape of the implant 20 can be formed into a circular shape. For example, as shown in the drawing, the three equally-spaced connection members 70 can be installed on the circumference.

Each of the above-described embodiments can be appropriately changed.

In the description of the embodiments, a method for introducing the implant 20 into the living body 120 by using the puncture tool 90 that has the inner needle 91 and the outer needle 96 has been described, but the method for introducing the implant 20 is not limited thereto, but can be appropriately changed insofar as the introduction into a predetermined part in the living body can be performed. For example, a method for puncturing and introducing the implant through a single process by using a puncture needle which has a body section into which the implant can be inserted and held can be adopted.

Also, the number of the layers constituting the implant 20 can be appropriately changed if the introduction region 41 into which the fluid is introduced can be partitioned around at least the first layer 30. For example, a plurality of layers such as a third layer, a fourth layer, and the like covering the second layer 40 can be further disposed without being limited to the two layers of the first layer 30 and the second layer 40 only. Materials of each of the additional layers can be appropriately selected from materials permeated or not permeated by the fluid flowing from the filling unit 31.

Also, it is possible to achieve an effect of the implant 20 reducing the load on the living body even when the implant 20 alone is placed. Accordingly, as described in the embodiments, the implant 20 alone can be used in procedures without using the implant assembly 10 assembled with the filling member 80.

Also, materials of the connection members 70 are not limited to what have been described in the embodiments but extensible materials such as sponge and a spring can be used instead of the thermally deformable metallic and resin materials.

Also, the site to which the implant 20 is applied is not limited to between the spinous processes 123 in the living body 120, but the implant 20 can be widely applied as the spacer that has the spacing function with respect to each organ in the living body.

What is claimed is:

1. An implant configured to be placed in a living body to be expansively deformed and contractively deformed, the implant comprising:

a first layer that forms a filling unit that is configured to be filled with a filling material to maintain an expanded state of the implant, the first layer comprising a porous membrane;

a second layer that covers the first layer, the second layer comprising at least one of (i) a fluid-impermeable membrane, and (ii) a gas-permeable porous membrane that is impermeable by liquids or gels;

a plurality of connection members that connect the first layer and the second layer with each other to position the first layer relative to the second layer; and an introduction port that communicates with the filling unit and is configured to introduce the filling material into the filling unit, wherein an introduction region is formed between the first layer and the second layer, the introduction region being configured to receive a fluid permeating the first layer when the filling material is introduced into the filling unit.

2. The implant according to claim 1,
wherein the filling material is a solid or a hardening material that is fluid at a time of the introduction into the filling unit and hardens after the introduction, and
the first layer is impermeable to the filling material.

3. The implant according to claim 1,
wherein at least one of a material constituting the first layer and a material constituting the second layer comprises a fiber material.

4. The implant according to claim 1,
wherein the second layer is coated with a water-swellable polymer material.

5. The implant according to claim 1,
wherein the first layer and the second layer are connected with each other by the introduction port.

6. The implant according to claim 1,
wherein the implant is configured such that, after expansive deformation, a body section and at least one wide section are formed in the implant, the wide section having a greater width than the body section, and
the plurality of connection members includes at least one of a body section side connection member that connects the first layer and the second layer with each other in the body section, and a wide section side connection member that connects the first layer and the second layer with each other in the wide section.

7. The implant according to claim 1,
wherein the connection members are disposed in pairs at opposing positions of the implant.

8. An implant assembly comprising:
the implant according to claim 1; and
a tubular member that includes a distal end section which is insertable into the filling unit of the implant via the introduction port, an opening section that is disposed in the distal end section to introduce the filling material into the filling unit, and a lumen that communicates with the opening section.

9. The implant assembly according to claim 8,
wherein a volume of the lumen of the tubular member is greater than or equal to a volume of the introduction region.

* * * * *